United States Patent
Wang et al.

(10) Patent No.: US 7,828,955 B2
(45) Date of Patent: Nov. 9, 2010

(54) AMMONIA GAS SENSORS

(75) Inventors: Da Yu Wang, Troy, MI (US); Walter T. Symons, Grand Blanc, MI (US); Robert J. Farhat, Grosse Pte Park, MI (US); Carlos A. Valdes, Flint, MI (US); Elizabeth M. Briggs, Chesterfield Township, MI (US); Kaius K. Polikarpus, Grand Blanc, MI (US); Joachim Kupe, Davisburg, MI (US)

(73) Assignee: Delphi Technologies, Inc., Troy, MI (US)

( * ) Notice: Subject to any disclaimer, the term of this patent is extended or adjusted under 35 U.S.C. 154(b) by 1156 days.

(21) Appl. No.: 11/483,448

(22) Filed: Jul. 10, 2006

(65) Prior Publication Data
US 2006/0266659 A1 Nov. 30, 2006

Related U.S. Application Data

(63) Continuation of application No. 10/734,018, filed on Dec. 11, 2003, now Pat. No. 7,074,319.

(60) Provisional application No. 60/432,601, filed on Dec. 11, 2002.

(51) Int. Cl.
*G01N 27/407* (2006.01)
(52) U.S. Cl. .................................. 205/780.5; 204/431
(58) Field of Classification Search .............. 205/780.5; 204/431, 432
See application file for complete search history.

(56) References Cited

U.S. PATENT DOCUMENTS

| 7,074,319 B2 * | 7/2006 | Wang et al. ............... 205/780.5 |
| 2003/0062264 A1 * | 4/2003 | Kitanoya et al. ............ 204/424 |

* cited by examiner

*Primary Examiner*—Alex Noguerola
(74) *Attorney, Agent, or Firm*—Thomas N. Twomey

(57) ABSTRACT

One embodiment of an ammonia gas sensor includes: a reference electrode, an ammonia selective sensing electrode and an electrolyte disposed therebetween. The sensing electrode comprises the reaction product of a main material selected from the group consisting of vanadium, tungsten, molybdenum, vanadium oxides, tungsten oxides, molybdenum oxides, and combinations comprising at least one of the foregoing main materials, and an electrically conducting material selected from the group consisting of electrically conductive metals, electrically conductive metal oxides, and combinations comprising at least one of the foregoing.

38 Claims, 8 Drawing Sheets

AMMONIA GAS SENSORS

CROSS REFERENCE TO RELATED APPLICATIONS

This application is a continuation of U.S. patent application Ser. No. 10/734,018, filed Dec. 11, 2003, now U.S. Pat. No. 7,074,319, and claims the benefit of U.S. Provisional Application No. 60/432,601, filed on Dec. 11, 2002, the teachings of which are incorporated herein by reference in their entirety.

BACKGROUND

Exhaust gas generated by combustion of fossil fuels in furnaces, ovens, and engines, for example, contains nitrogen oxides ($NO_X$), unburned hydrocarbons (HC), and carbon monoxide (CO). Automobile gasoline engines utilize various pollution-control after treatment devices such as, for example, a three-way catalyst converter to reduce and oxidize $NO_X$, CO, and HC. The $NO_X$ reduction is accomplished by using ammonia gas ($NH_3$) supplied by a urea tank, or by using HC and CO, which is generated by running the engine temporarily in rich conditions. The overall reaction for converting urea to ammonia is:

$$NH_2CONH_2 + H_2O(steam) \rightarrow 2NH_3 + CO_2 + H_2O.$$

The product gas is a mixture of ammonia gas, carbon dioxide ($CO_2$), and water vapor. In order for urea-based catalysts and trap technologies to work efficiently, and to avoid pollution breakthrough, an effective feedback control loop is needed to manage the regeneration cycle of the $NO_X$ traps. To develop such control technology, there is an ongoing need for an economically-produced and reliable commercial ammonia sensor.

A need also exists for a reliable ammonia sensor for air ammonia monitoring in agricultural plants where ammonia present in animal shades, and in all other industries wherein ammonia is produced or used or is a by-product. Commercially available sensors typically suffer from lack of high sensitivity and selectivity. Thus, a widespread need exists for an improved ammonia gas sensor.

SUMMARY

In accordance with this invention, an ammonia gas sensor comprises an electrolyte, a reference electrode in contact with the electrolyte, and an ammonia selective sensing electrode in contact with the electrolyte spaced apart from the reference electrode. The ammonia selective sensing electrode is composed of an oxide material characterized by the formula

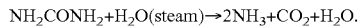

wherein M is selected from the group consisting of vanadium, tungsten, and molybdenum; A is one or more metals; and x, y and z are numbers indicative of the atomic proportion.

The electrolyte is composed of a material capable of electrochemical transfer of hydrogen ions. A suitable electrolyte is a zirconia composition. The zirconia composition may contain an additive adapted to stabilize the zirconia at elevated temperatures. A preferred electrolyte is yttria-stabilized zirconia.

Referring to the aforementioned formula, A may be bismuth, lead, lanthanum, strontium, calcium, copper, gadolinium, neodymium, yttrium, samarium, or magnesium. A may be between about 0.1 at % to about 15 at % (x between 0.01 and 0.15), more suitably between about 1 at % to about 10 at % (x between 0.01 and 0.1), and preferably between about 3 at % to about 8 at % (x between 0.03 and 0.08). The oxide material may further comprise a chemically stabilizing dopant, such as tantalum, niobium, or magnesium, in an amount between about 0.1 at % to about 5 at %, preferably between about 0.3 at % to about 3 at %. Further, the oxide material may contain a diffusion-impeding dopant, such as zinc, zirconium, lead, iron, or yttrium. In a preferred embodiment, M is vanadium and A is selected from the group consisting of bismuth, lead, lanthanum, strontium, calcium, copper, gadolinium, neodymium, yttrium, samarium, magnesium, tin, antimony, neodymium, tantalum and chromium. By way of a preferred oxide material, M is vanadium; and A is bismuth; and the oxide material optionally includes tantalum or magnesium as a chemically stabilizing dopant, and/or zinc, zirconium, lead, iron, and yttrium as a diffusion-impeding dopant.

In one aspect of this invention, a process for measuring the concentration of ammonia in a gas is provided using an ammonia gas sensor in accordance with the above description. The gas to be measures is contacting with the ammonia selecting sensing electrode; and a voltage signal is measured between said ammonia sensing electrode and said reference electrode.

BRIEF DESCRIPTION OF DRAWINGS

Referring now to the figures, which are exemplary embodiments, and wherein the like elements are numbered alike.

DETAILED DESCRIPTION

Figure 1:
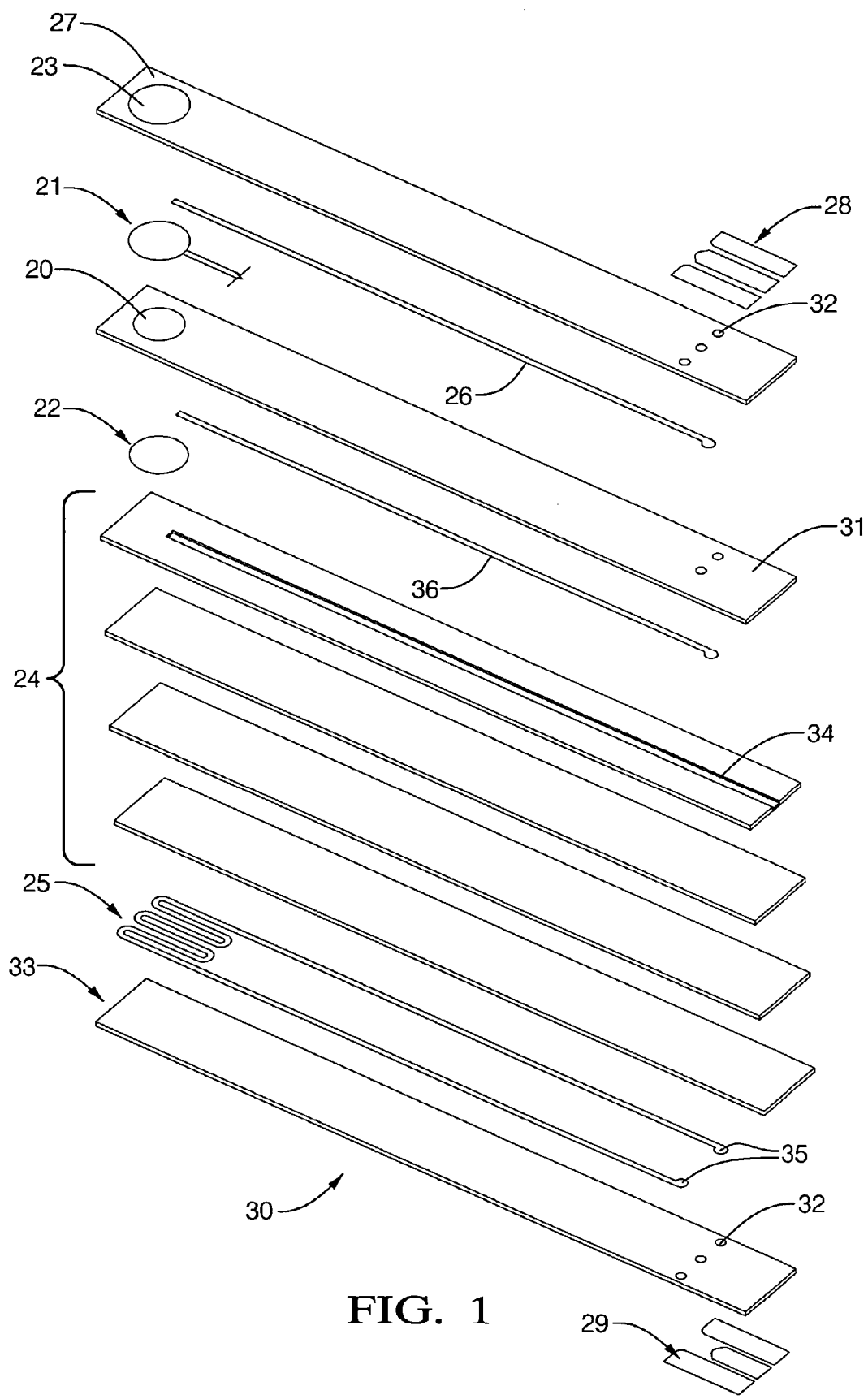
FIG. 1 is a schematic partial cutaway view of an ammonia gas sensor with the layers separated.

The present disclosure relates to an ammonia sensor for monitoring and measuring ammonia gas in a gas stream such as exhaust gases in combustion systems, for example, internal combustion engines and furnaces. It is noted that, although the sensor is described in relation to a flat plate sensor, other sensor designs can also be employed, such as conical and the like.

An ammonia gas sensor may employ a pair of electrodes disposed on opposite sides of an electrolyte (e.g., yttria ($Y_2O_3$) stabilized zirconia ($ZrO_2$)) element. One of the electrodes, referred to herein as a reference electrode, is typically surrounded by a gas having a predetermined ammonia concentration or by ambient air, to the same gas of which the $NH_3$ amount needs to be sensed. The other electrode, referred to herein as a sensing electrode, is exposed to the gas being monitored or tested for its concentration of ammonia. The gas being tested or monitored is referred to herein as the sensing gas. Therefore, when the concentration of ammonia molecules is greater at one of the electrodes than at the other, an electron imbalance will occur at the respective electrodes, and a voltage is generated between the electrodes. In the case where the reference electrode is also exposed to the sensing gas, the reference electrode comprises materials (e.g., platinum (Pt), and the like) that will catalytically equilibrate the $NH_3$ with the oxygen, leaving no $NH_3$ on the reference electrode electrochemical active area. In such a situation, the $NH_3$ activity difference between the two electrodes will produce the emf. The output voltage is a function of the partial pressures of ammonia in the sensing gas, as well as the temperature of the electrolyte. The voltage generated between the two electrodes is defined by the so-called "Nernst" equation.

The Nernst equation can be used to calculate the actual reversible potential of an electrode (measured in volts), E, in relation to the standard reversible potential of the electrode couple, E°, which is a thermodynamic value at standard conditions, 298° K and 1 atmosphere pressure. Nernst equation, for a reaction involving only gaseous species, can be written as:

$$E = E^0 - \left(\frac{RT}{zF}\right) \times \ln\left(\frac{P_1}{P_2}\right) + C$$

wherein:
E=electromotive force;
T=the absolute temperature of the sensor in degrees Kelvin (° K);
R=the Universal Gas Constant=8.3145 Joule per mole-° K (J/(mole-° K));
z is the charge number of the electrode reaction (i.e., the number of moles of electrons involved in the reaction as written);
F=Faraday's Constant=96,500 coulombs/mole;
$P_1$=the partial pressure in atmospheres, of ammonia in the reference gas;
$P_2$=the partial pressure, in atmospheres, of the monitored gas (sensing gas);
C=a constant for each individual sensor; and $$\ln\left(\frac{P_1}{P_2}\right)$$

is the natural logarithm of the ratio $$\left(\frac{P_1}{P_2}\right).$$

For a concentration cell such as the cell employed in the ammonia sensor, z=1 and E°=0.

Thus, the Nernst equation for a concentration cell used to sense ammonia can be written as:

$$E = -\left(\frac{RT}{F}\right) \times \ln\left(\frac{P_1}{P_2}\right) + C$$

The ammonia gas sensor can comprise two electrodes that are used together with an electrolyte. One electrode, the reference electrode, can be exposed to a reference gas, e.g., air ambient air or even the gas to be sensed. The other electrode, the sensing electrode, can be exposed to the gas to be monitored (i.e., the sensing gas), and therefore comprises materials that are selectively sensitive to ammonia and preferably not sensitive to nitrogen oxides ($NO_x$), carbon monoxide (CO), and hydrocarbons (HC), wherein not sensitive means that the sensor output (e.g., millivolts (mV)) in the presence of $NH_3$ is substantially the same in the presence of $NH_3$, NOx, HCs, and CO (i.e., within about ±5%). In other words, when a gas comprising 100 ppm $NH_3$ is tested, a sensor reading of 140 mV may be obtained. When the same sensor is used to sense a gas comprising 100 parts per million (ppm) $NH_3$, 1,000 ppm NOx, 100 ppm HC, and 100 ppm CO, the sensor output voltage will be about 133 mV to about 147 mV. As used herein, unless otherwise specified, ppm is by weight and based upon the total weight of the gas. Essentially, the difference between the two electrodes causes an electromotive force to be generated when the sensor is placed in a gas stream containing ammonia gas. The resultant electrical potential is a function of the ammonia concentration. As described above, the sensing function is based on non-equilibrium Nernstian electrochemical principles.

Referring now to FIG. 1, a schematic cutaway view of a sensor 30 is shown to comprise a sensor protective layer 27 with a porous portion 23, which can allow a sensing gas to diffuse through to reach the outer electrode, and a sensing electrode 21 that is in ionic communication with an electrolyte 20 and electrical communication with vias 32 through sensor lead 26. Sensor protective layer 27 is located between contact pads 28 and sensor lead 26. The sensing electrode 21 can be exposed to the gas to be sensed, e.g., the gas stream or sensing gas. On the side of the sensing electrode 21 opposite the protective layer 27, is an electrolyte layer 31 comprising an electrolyte 20. On the other side of electrolyte 20 is the inner electrode, i.e., a reference electrode 22. On a side of the reference electrode 22, opposite the electrolyte layer 31, is a reference gas channel 34 (and/or a chamber (not shown) for reference gas) in fluid communication with the reference channel. In the case, where the sensing gas is also used as the reference gas, the channel 34 will open (e.g., to the side) to access the sensing gas. Between the reference electrode 22 and the associated reference lead 36 and a heater 25 are one or more insulating layers 24. Optionally, a temperature sensor (not shown) may be disposed between layers 24 for control of the heater 25, and/or a ground plane (not shown) may be disposed therebetween. The heater 25, which is disposed in thermal communication with the sensing end of the sensor (i.e., the end comprising the electrodes 21, 22), is preferably located between the insulating layers 25 and a heater protective layer 33. On the outside of the sensor element 30, on a side of the heater protective layer 33, are contact pads 29 in electrical communication with vias 32 that are in electrical communication with the heater leads 35.

The sensing electrode 21 may comprise any ammonia selective material compatible with the operating environment. Possible electrode materials include vanadium (V), tungsten (W), molybdenum (Mo), vanadium oxides, tungsten oxides, and/or molybdenum oxides, and the like, in combination with electrically conductive metals and/or metal oxides. Some such materials include vanadium pentoxide ($V_2O_5$), bismuth vanadium oxide ($BiVO_4$), copper vanadium oxide ($Cu_2(VO_3)_2$), tungsten oxide ($WO_3$), and/or molybdenum oxide ($MoO_3$), with electrically conductive metals and/or metal oxides; $V_2O_5$, with CaO, SrO, SnO, CuO, PbO, $Sb_2O_3$, $Bi_2O_3$, $Nb_2O_5$, $Ta_2O_5$, $CrO_3$, $WO_3$, and/or $MoO_3$, and with electrical conducting metal and metal oxide materials as the electrode materials; as well as combinations of the foregoing materials. Possible electrical conducting metals that can be employed comprise Pd, Pt, Au, and the like, as well as alloys and combinations comprising at least one of the foregoing conducting metals, while possible electrical conducting metal oxides comprise oxides of bismuth (Bi), lead (Pb), magnesium (Mg), lanthanum (La), strontium (Sr), calcium (Ca), copper (Cu), gadolinium (Gd), neodymium (Nd), yttrium (Y), samarium (Sm), such as $Ba_2O_2$, CaO, $Cu_2O$, $Ba_2CaCu_2$ oxide, BiPbSrCaCu oxide, $Ba_2Cu_3$ oxide, LaSr (Co, Fe, In, Ti, and/or Mn) oxide (e.g., LaSrCu oxide, and the like), LaCo oxide, BiSrFe oxide, and the like, with oxides of Bi preferred.

In one embodiment, the sensing electrode comprises vanadium oxide doped with an electrically conductive metal and optionally a chemical stabilizing metal. When the vanadium oxide is doped with the electrically conductive metal, that metal replaces the vanadium in the oxide. For instance, when $Bi_2O_3$ is combined with $V_2O_5$ and fired, a new material is formed having the formula $BiVO_4$. Basically, the Bi has replaced some of the V in the formulation. In this formulation (i.e., $BiVO_4$), the Bi (or other electrically conducting metal (s)/oxide(s)) is present in about 0.1 at % to about 15 at %. Within this range, the amount of electrically conducting metal can be greater than or equal to about 0.1 at %, with greater than or equal to about 1 at % preferred, and greater than or equal to about 3 at % more preferred. Also preferred is an amount of electrically conducing metal of less than or equal to about 15 at %, with less than or equal to about 10 at % preferred, and less than or equal to about 8 at % more preferred. When the formulation is further doped with a chemically stabilizing metal(s)/dopant(s) (e.g., tantalum (Ta), niobium (Nb), Mg, and the like, as well as oxides and combinations comprising at least one of these dopants), the chemically stabilizing metal replaces some of the V in the formulation, while the diffusion-impeding dopant(s) (e.g., zinc (Zn), iron (Fe), zirconium (Zr), lead (Pb), yttrium (Y), and/or the like, as well as combinations comprising at least one of these dopants) replace some of the Bi in the formulation; to produce $BiTaZrPbYVO_4$, $BiMgZnPbYZrVO_4$, $BiZnZrVO_4$, $BiZnPbYVO_4$, or the like. All atomic percents are based upon the amount of the component in the formula.

In these examples, the chemical stabilizing dopant(s), which help to eliminate the green effect, can be present in an amount of about 0.1 to about 15 at %. Meanwhile, the diffusion impeding dopant(s), which helps to inhibit poisoning of the electrode by contaminants such as Pb, Zr, Zn, Fe, and Y, the chemically stabilizing metal(s) can be collectively present in an amount of about 0.1 at % to about 5 at %. Within this range, the collective amount of the chemically stabilizing metal(s) is less than or equal to 5 at %, with less than or equal to about 3 at % preferred, and less than or equal to about 1 at % more preferred. Also preferred within this range is a collective amount of the chemically stabilizing metal(s) of greater than or equal to 0.1 at %, with greater than or equal to about 0.3 at % preferred, and greater than or equal to about 0.5 at % more preferred.

The formulation for the sensing electrode 21 can be formed in advance of deposition onto the electrolyte 20 or can be disposed on the electrolyte 20 and formed during the firing of the sensor. For example, a typical oxygen sensing electrode formulation can be disposed on the electrolyte 20 (the "initial formulation"). A layer (e.g., sprayed, painted, dipped, screen printed, laminated, and/or the like) can be placed over the initial formulation. The layer comprises the main material (i.e., vanadium (V), tungsten (W), molybdenum (Mo), vanadium oxides, tungsten oxides, and/or molybdenum oxides, and the like, with vanadium oxide preferred), the conducting metal/oxide (e.g., Bi, Pb, La, Sr, Ca, Cu Gd, Nd, Y, Sm, and/or the like), the chemically stabilizing metal(s) (e.g., Mg, Ta, and/or the like), and diffusion-impeding dopants (e.g., Zr, Fe, Zn, Pb, Y, and/or the like) and oxygen. When the sensor is fired, these react with each other and with the initial formulation to form a reaction product, the sensing electrode.

Due to the inconsistency (lack of repeatability) of the above process, it is preferably to first prepare the sensing formulation and then dispose it onto the electrolyte (or the layer adjacent the electrolyte). In this method, the main material, preferably in the form of an oxide, is combined with the other metals/oxides simultaneously or in sequentially. By either method, the materials are preferably well mixed to enable the desire replacement of the main metal and/or conducting metal in the formulation to produce the desired sensing electrode. For example, $V_2O_5$ is mixed with $Bi_2O_3$ and $Ta_2O_5$ by milling for about 2 to about 24 hours. The mixture is fired to about 800° C. to about 900° C. for a sufficient period of time to allow the metals to transfer into the vanadium oxide structure and produce the new formulation (e.g., $BiTa_{0.5}V_{0.95}O_{4-x}$, (wherein x is the difference in the value between the stochiometric amount of oxygen and the actual amount)), which is the reaction product of the main material, electrically conductive material, chemical stabilizing dopant, and/or diffusion impeding dopant. The period of time is dependent upon the specific temperature and the particular materials, but may be about 0.5 hours to 24 hours or so. Once the sensing formulation has been prepared, it can be made into an ink and disposed onto the desired sensor layer.

If an ink is employed, beside the above metals/oxides/dopants, it may also comprise binder(s), carrier(s), wetting agent(s), and the like, and combinations comprising at least one of the foregoing. The binder may be any material capable of providing adhesion between the ink and the substrate. Suitable binders include acrylic resin, acrylonitrile, styrene, acrylic acid, methacrylic acid, methyl acrylate, methyl methacrylate, and the like, as well as combinations comprising at least one of these binders. The carrier may include any material suitable for imparting desired printing and drying characteristics of the ink. In general, the carrier includes a polymer resin dissolved in a volatile solvent. The wetting agent may include ethanol, isopropyl alcohol, methanol, cetyl alcohol, calcium octoate, zinc octoate and the like, as well as combinations comprising at least one of the foregoing. For example, the ink may comprise about 10 weight percent (wt %) to about 30 wt % 1-methoxy-2-propanol acetate solvent, about 10 wt % to about 30 wt % butyl acetate solvent, about 5 wt % to about 10 wt % acrylic resin binder, 0 to about 5 wt % (e.g., 0.1 wt % to about 5 wt %) methyl methacrylate polymer, about 5 wt % to about 10 wt % ethanol wetting agent, and about 30 wt % to about 60 wt % of the sensing formulation, based upon the total weight of the ink.

In contrast to the sensing electrode 21, the reference electrode 22 can comprise any electrode material, i.e., it does not need to be sensitive to $NH_3$. The reference electrode 22 can comprise any catalyst capable of producing an electromotive force across the electrolyte 20 when the sensing electrode 21 contacts $NH_3$, including metals such as platinum, palladium, gold, osmium, rhodium, iridium, ruthenium, zirconium, yttrium, cerium, calcium, aluminum, and the like, as well as alloys, oxides, and combinations comprising at least one of the foregoing catalysts. A catalyst comprising platinum is preferred due to platinum having a processing temperature as high the ceramic parts (1,400° C. and above), and being readily commercially available as an ink.

Fugitive materials can also be employed in the electrode formulations to enable the desired porosity of the final electrodes, e.g., preferably a sufficient porosity to enable the ammonia to enter the electrode and reach triple points (points where the electrode, electrolyte, and ammonia meet to enable the desired reactions). Fugitive materials, i.e., materials that degrade leave voids upon firing. Some possible fugitive materials include graphite, carbon black, starch, nylon, polystyrene, latex, other soluble organics (e.g., sugars and the like) and the like, as well as compositions comprising one or more of the foregoing fugitive materials.

With respect to the size and geometry of the sensing and reference electrodes 21, 22, they are generally adequate to provide current output sufficient to enable reasonable signal resolution over a wide range of ammonia concentrations. Generally, a thickness of about 1.0 micrometers to about 25 micrometers can be employed, with a thickness of about 5 micrometers to about 20 micrometers preferred, and about 10 micrometers to about 18 micrometers more preferred. The geometry of the electrodes is preferably substantially similar to the geometry of the electrolyte.

Electrodes can be formed using techniques such as chemical vapor deposition, screen printing, sputtering, and stenciling, among others, with screen printing the sensing and reference electrodes onto appropriate tapes being preferred due to simplicity, economy, and compatibility with the subsequent firing process. For example, reference electrode 22 can be screen printed onto support layer 24 or over the electrolyte 20, and the sensing electrode 21 can be screen printed under porous protective layer 23 or over the electrolyte 20.

Electrode leads 26, 36 (as well as heater leads) and vias 32 in the layers 27, 31, 33 are typically formed simultaneously with electrodes. However, if the sensor element 30 is not co-fired (i.e., all of the green layers laid up to form the green sensor, and the green sensor then fired to form the final sensor), the vias 32 and leads 26, 36 can be formed separately from the electrodes 21, 22. In this embodiment, when the electrodes 21, 22 comprise material(s) that can not be heated to the sintering temperatures without degrading the electrodes 21, 22, the electrodes 21, 22 can be screen printed onto the sintered layer(s) and then fired at a lower temperature to activate the materials.

Although the porosity of reference electrode 22 is typically sufficient to hold an adequate quantity of ammonia to act as a reference, a space for storing reference ammonia (not shown) can be provided between reference electrode 22 and adjoining support layer 24. This space can be formed by depositing a fugitive material between the reference electrode 22 and the adjacent insulating layer such that upon processing the fugitive material burns out leaving a void. Alternatively, reference electrode 22 can be in fluid communication with a point external to the sensor allowing reference gas access to the reference electrode via a channel 34 in layer.

Disposed between the electrodes 21, 22 is an electrolyte 20, which is preferably a solid electrolyte that can comprise the entire layer 31 or a portion thereof. The electrolyte 20 can be any material that is capable of permitting the electrochemical transfer of hydrogen ions while inhibiting the physical passage of exhaust gases, has an ionic/total conductivity ratio of approximately unity, and is compatible with the environment in which sensor element will be utilized (e.g., up to about 1,000° C.). Possible electrolyte materials can comprise metal oxides such as zirconia, and the like, which may optionally be stabilized with calcium, barium, yttrium, magnesium, aluminum, lanthanum, cesium, gadolinium, and the like, and oxides thereof, as well as combinations comprising at least one of the foregoing electrolyte materials. For example, the electrolyte can be alumina and yttrium stabilized zirconia. Typically, the electrolyte has a thickness of up to about 500 micrometers, with a thickness of approximately 25 micrometers to about 500 micrometers preferred, and a thickness of about 50 micrometers to about 200 micrometers especially preferred for planar sensors.

Electrolytes 20 can be formed via many processes including, but not limited to, slurry doctor blade, die pressing, roll compaction, stenciling, and screen printing, and the like. For improved process compatibility, it is preferred to utilize a tape process using known ceramic tape casting methods. If the electrolyte 20 comprises a portion of the electrolyte layer 31, a stamping method may also be employed where the electrolyte is disposed into an opening in the electrolyte layer 31 or attached onto an end of the electrolyte layer 31.

Disposed on a side of the reference electrode 22, opposite the electrolyte 20, can be one or more insulating layers 24, (e.g., dielectric layers), a heater protective layer 33, and a sensor protective layer 27. These layers comprise materials that effectively protect various portions of the sensor element 30, provide structural integrity, and separate various components. Heater protective layer 33 electrically isolates the heater 25 from the sensor circuits, while support layers 24 physically separate the reference electrode 22 and heater 25, and the sensor protective layer 27 protects the sensor 21 and sensor lead 26 from abrasion and contaminants, and provides electrical insulation. Preferably these layers comprise alumina or similar insulating materials that are compatible with the electrolyte and the operating environment, and which are chosen to at least minimize, if not eliminate, delamination and other processing problems.

The insulating layers 24 and protective layers 27, 33, can each be up to about 200 micrometers thick or so, depending upon the number of layers employed, with a thickness of about 50 micrometers to about 200 micrometers preferred. As with the electrolyte layer 31, these layers can be formed using ceramic tape casting methods or other methods such as plasma spray deposition techniques, screen printing, stenciling and others.

The protective layer 27 can comprise a porous portion 23 that has a sufficient porosity to allow the ammonia to pass therethrough, while protecting the electrode from abrasion, particulates, and the like. Possible materials for the porous portion include aluminum oxides, magnesium aluminate, spinel, and the like, as well as combinations comprising at least one of the foregoing materials.

Disposed between the insulating layers 24 and the heater protective layer 33, is the heater 25, with a ground plane (not shown) and/or a temperature sensor (not shown) optionally disposed between two other substrate layers. The heater 25 can be any heater capable of maintaining a sensor end of sensor element 30 at a sufficient temperature to facilitate the various electrochemical reactions therein. The heater, which can be platinum, palladium, aluminum, and the like, or alloys or combinations comprising at least one of the foregoing, or any other heater compatible with the environment, is generally screen printed onto a substrate to a thickness of about 5 micrometers to about 50 micrometers or so.

Leads 26, 35, 36 are disposed across various dielectric layers to electrically connect the external wiring of sensor element 30 with electrodes 21, 22. Leads are typically formed on the same layer as the electrode and heater to which they are in electrical communication and extend from the electrode/heater to the terminal end of the element (i.e., the end opposite the sensing end) where they are in electrical communication with the corresponding via 32.

At terminal end of sensor element, vias 32 are formed as holes filled with electrically conductive material in the appropriate layers or can be a hole at the end of the layer providing electrical communication through the layer. Vias are typically filled during formation of electrodes/heater 21, 22, 25 and leads 26, 35, 36, and serve to provide a mechanism for electrically connecting leads 25, 35, 36 to contact pads 28, 29 on the exterior of sensor element 30. These contact pads 28, 29 provide a contact point for the external sensor circuit.

The disclosed sensors can be built by bulk ceramic technology, or thick-film multi-layer technology, or thin-film multi-layer technology. In bulk ceramic technology, the sensors are formed in a cup shape by traditional ceramic processing methods with the electrodes deposed by ink methods (e.g., screen printing) and/or plasma method. During formation, essentially, the respective electrodes, leads, heater(s), optional ground plane(s), optional temperature sensor(s), optional fugitive material(s), vias, and the like, are disposed onto the appropriate layers. The layers are laid-up accordingly (e.g., as illustrated in FIG. 1), and then fired at temperatures of about 1,400° C. to about 1,500° C. Alternatively, the electrodes are not disposed onto the layers. The green layers (including the leads, optional ground plane(s), optional temperature sensor(s), optional fugitive material(s), vias, and the like) are fired at temperatures sufficient to sinter the layers, e.g., temperatures of about 1,400° C. to about 1,500° C. The electrodes are then disposed on the appropriate fired layer(s), and the layers are laid-up accordingly. The sensor element is then again fired at a temperature sufficient to activate the electrode materials, e.g., temperatures of about 700° C. to about 850° C.

Figure 2:
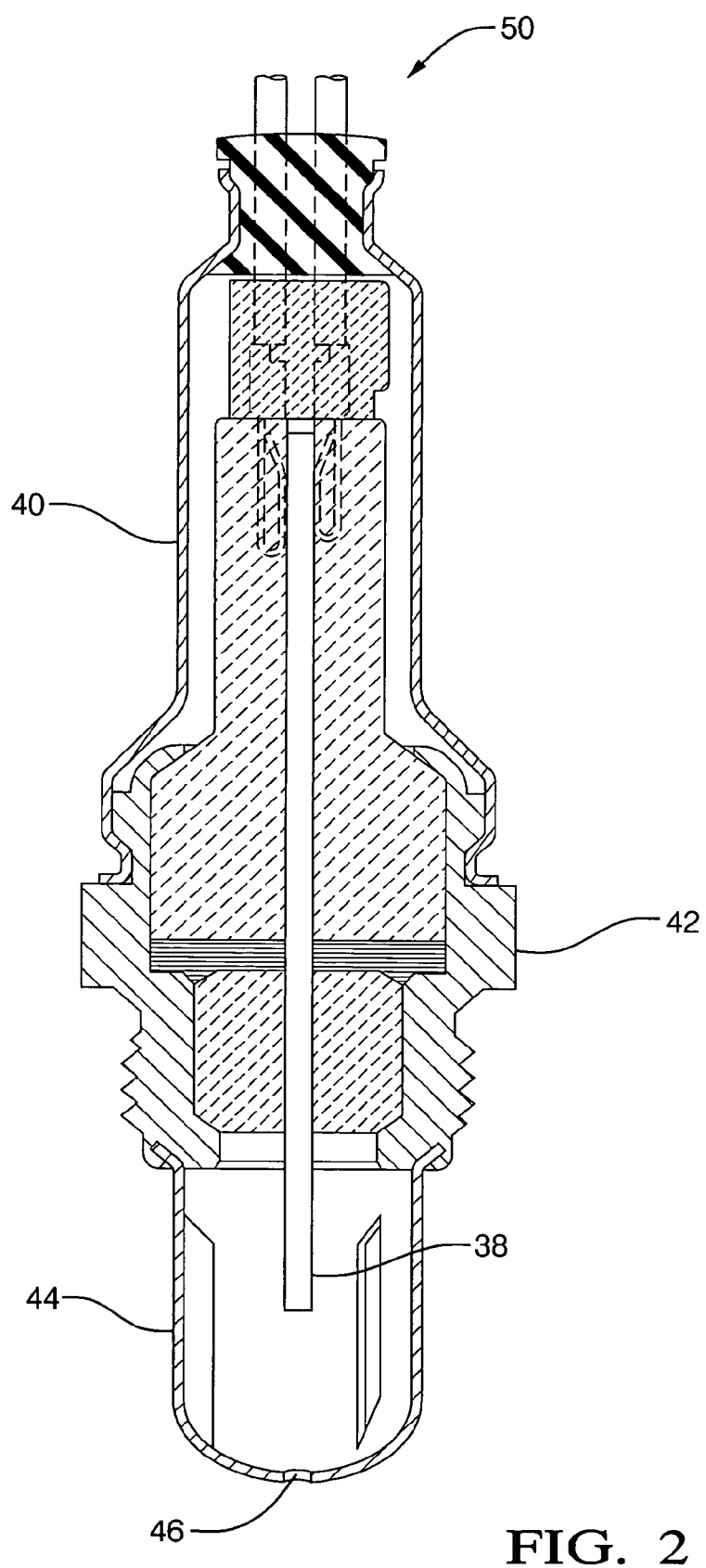
FIG. 2 is a cutaway view of an ammonia gas sensor package comprising sensor 

Referring now to FIG. 2, the sintered sensor element 38 is disposed in a housing or package to form the completed sensor 50. The sensor 50 comprises a the sintered sensor element 38, an upper shell 40, a lower shell 42, and a lower shield 44. The sensor element 38 extends from the upper shell 40, through the lower shell 42, and into the lower shield 44. The lower shield 44 has opening(s) 46 to enable fluid communication between the sensing end of the sensor element 38 and the gas to be sensed. To provide structural integrity to the sensor element 38, insulators 62 (e.g., ceramic, talc, mesh (metal or other), and/or the like) are disposed between the sensor element 38 and the shell 40, 42. The terminal end of the sensor 38 is disposed within upper shell 40 in electrical commutation with a terminal interface 48 such that cables 52 can be disposed in electrical communication with the sensor 38 via the contact pads.

During operation, the ammonia sensor is disposed in an area where a gas is to be sensed (e.g., within an exhaust conduit of a vehicle). When a gas passes down the conduit, the gas enters the sensor 50 through opening 46 and contacts the sensor element 38. The gases pass through the porous protective layer 23 where they contact the sensing electrode. Due to the ammonia concentration at the sensing electrode 21 and the insensitivity to the ammonia at the reference electrode 22, ammonia concentration is detected in the gas stream. This information can be fed to an analyzer that is in operable communication with the vehicle. Based upon the ammonia concentration, the introduction of ammonia, urea, and/or the air to fuel ratio of the exhaust stream can be adjusted to attain the desired emissions.

The following examples are intended to further describe the ammonia sensor and electrodes thereof and not to limit the present disclosure.

EXAMPLES

Examples 1-12 illustrate one type of ammonia selective sensing electrode comprising $V_2O_5$ with electrical conducting metal and/or metal oxide materials. For examples 3-, the sensor was exposed to $NO/NO_2$, $C_3H_6/C_3H_8$, CO, and $NH_3$ gases in sequence, with the background gas being $N_2$ mixed with 1.5 volume percent (vol %) $H_2O$ and 14-17 vol % of $O_2$.

Example 1

Au and $V_2O_5$ pastes were printed together and were fired at 750° C. for 10 minutes. Afterwards, the sensing elements were operated with a 9 volt (V)-0.84 amperes (amp) (7.56 watt (W)) power supplied to the heater. The sensor was exposed for 25 minutes to the gases $NO/NO_2$, $C_3H_6/C_3H_8$, CO, and $NH_3$, in sequence. The background gas was $N_2$ mixed with 1.5 vol % $H_2O$ and 14-17 vol % $O_2$. The results are shown in FIG. 3.

Figure 3:
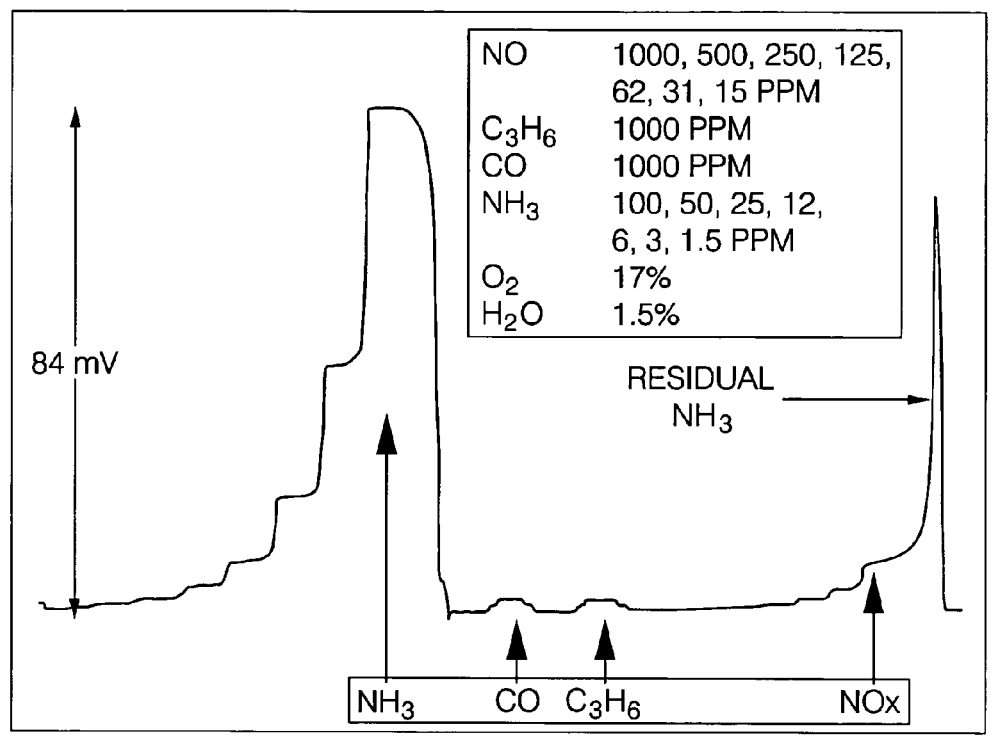
FIG. 3 is a graphical representation of the results of testing the ammonia gas sensor described in Example 1.

The curve shown in FIG. 3 is read from left to right in time sense. The initial rise in the curve before the $NO/NO_2$ response is due to residual $NH_3$ in the gas line. The concentrations of the individual gases were NO—1,000 per million ppm, 500 ppm, 250 ppm, 125 ppm, 62 ppm, 31 ppm, 15 ppm; $C_3H_6$—1,000 ppm; CO—1,000 ppm; $NH_3$—100 ppm, 50 ppm, 25 ppm, 12 ppm, 6 ppm, 3 ppm, 1.5 ppm (based upon the total of the combined gases); $O_2$—17 vol %; and $H_2O$—1.5 vol %, based upon the total volume of the gases. As used herein, ppm is by weight unless otherwise specified.

Example 2

$La_{0.79}Sr_{0.2}FeO_x$ and $V_2O_5$ pastes were printed together and were fired at about 750° C. for 10 minutes. Afterwards, the sensing elements were operated with the 6.5 V-1.41 amp (9.165 W) power supplied to the heater. The sensor was exposed for 25 minutes to $NO/NO_2$, $C_3H_6/C_3H_8$, CO, and $NH_3$ gas in sequence. The background gas was $N_2$ mixed with 1.5 vol % $H_2O$ and 14-17 vol % of $O_2$, based upon the total volume of the gases. The results are shown in FIG. 4.

Figure 4:
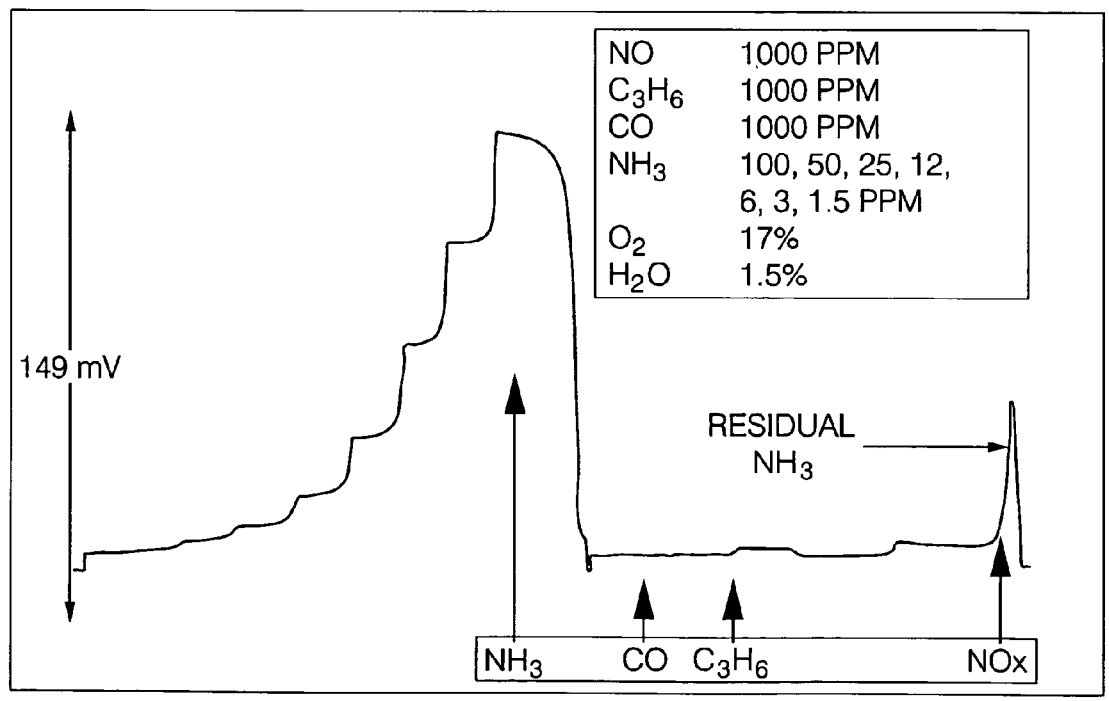
FIG. 4 is a graphical representation of the results of testing the ammonia gas sensor described in Example 2.
Figure 5:
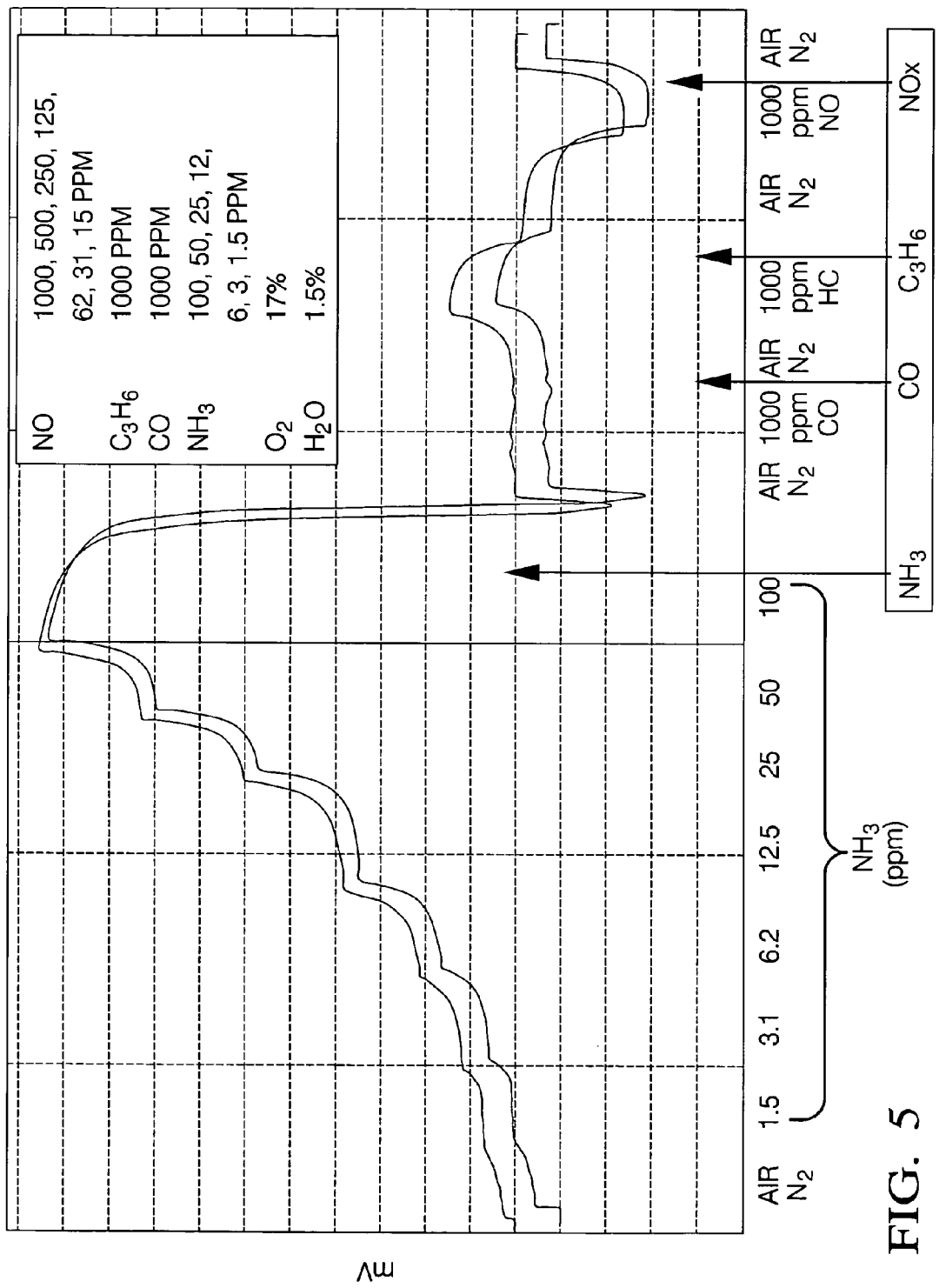
FIG. 5 is a graphical illustration of the results of exposing two sensors (comprising $V_2O_5$ with 0.5 mole % doping of aliovalent species and thermally treated at 850° C. for 4 hours) to $NO/NO_2$, $C_3H_6/C_3H_8$, CO, $NH_3$ gas in sequence, with the background gas being $N_2$ mixed with 1.5 mole % $H_2O$ and 14-17 mole % of $O_2$, wherein the measurement was done on gas bench at 550° C.
Figure 6:
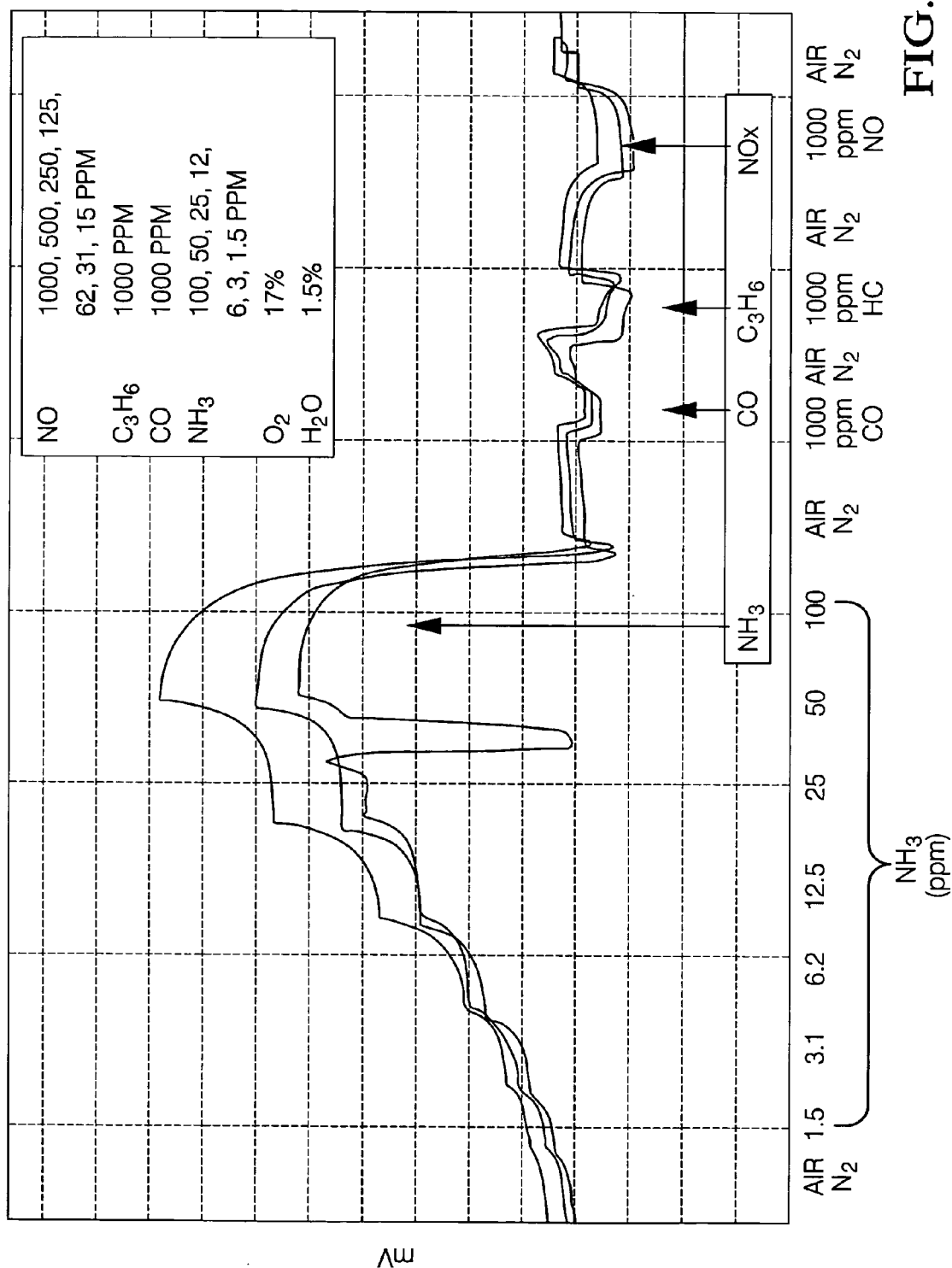
FIG. 6 is a graphical illustration of the results of exposing three sensors (comprising $V_2O_5$ mixed with $Ce_{(0.8)}Sm_{(0.2)}O_2$ (1:1 atomic ratio) and thermally treated at 850° C. for 4 hours) to $NO/NO_2$, $C_3H_6/C_3H_8$, CO, $NH_3$ gas in sequence, with the background gas being $N_2$ mixed with 1.5 mole percent (mol %) $H_2O$ and 14-17 mol % of $O_2$, wherein the measurement was done on gas bench at 550° C.
Figure 7:
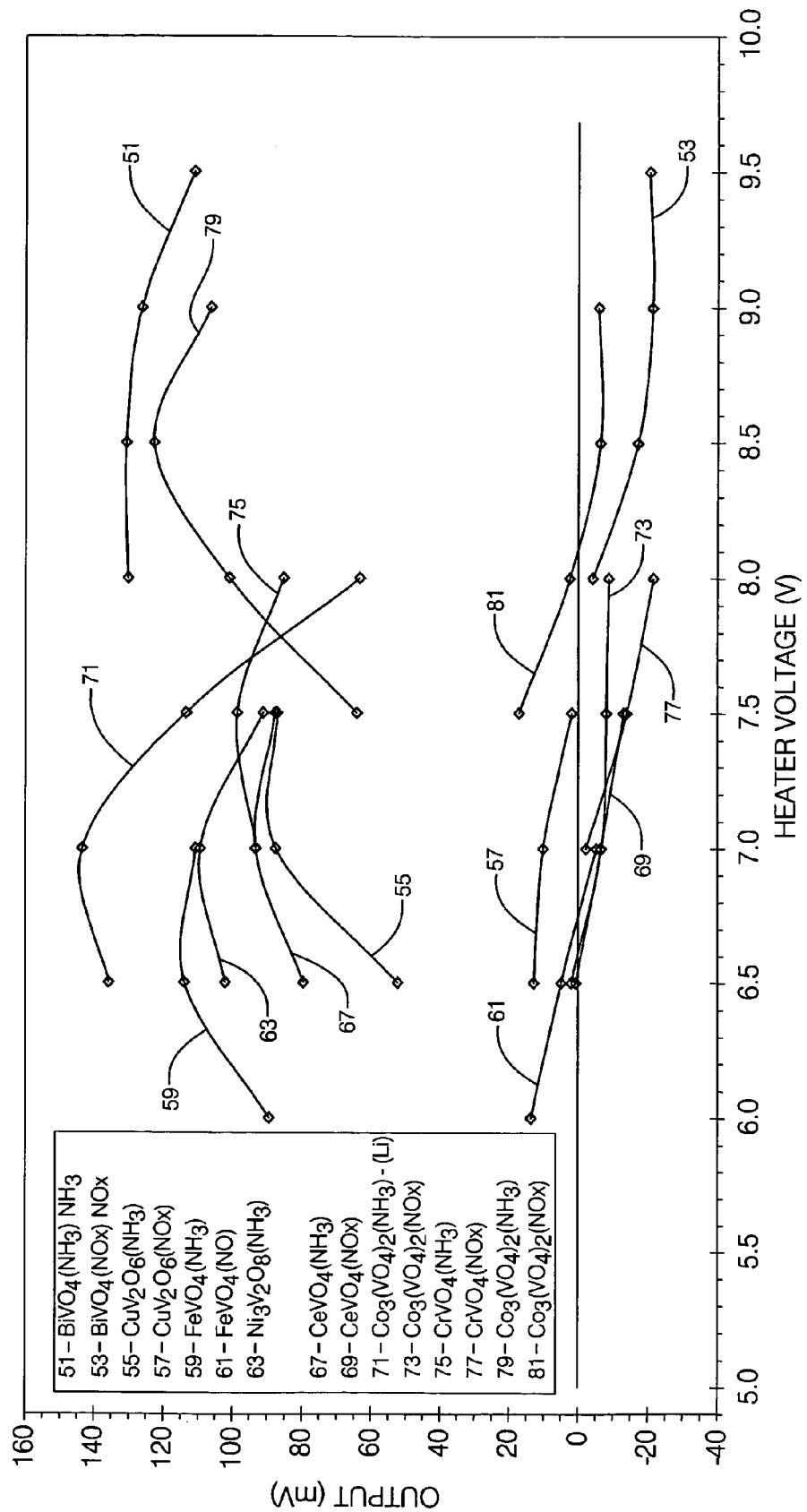
FIG. 7 is a graph illustrating, in the top curves, sensor emf outputs as function of heater voltage for a 100 ppm $NH_3$ gas mixture (100 ppm of $NH_3$, 14.7 mol % $O_2$ and 1.5 mol % $H_2O$, balance $N_2$), while the lower curves illustrate sensor emf outputs as function of heater voltage for a 1,000 ppm NOx gas mixture (1,000 ppm NOx, 14.7 mol % $O_2$, 1.5 mol % $H_2O$, balance $N_2$)
Figure 8:
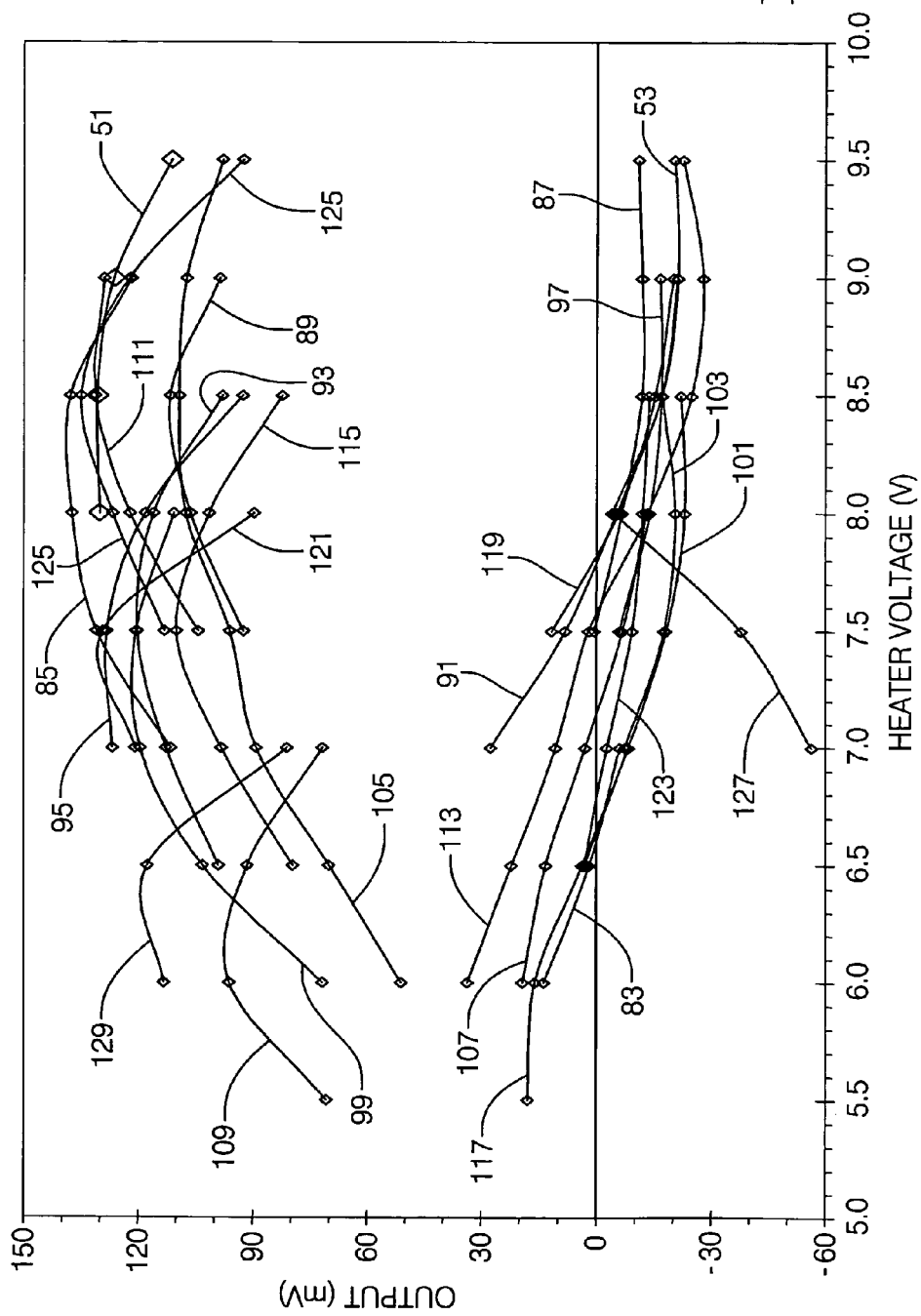
FIG. 8 is a graphical illustration of sensor emf outputs as function of heater voltage, with the top curves, again, for 100 ppm $NH_3$ response, and the lower curves for 1,000 ppm NOx gas mixtures, for vanadium pentoxide that has been doped with various dopants.

The curve shown in FIG. 4 is read from left to right in time sense. The initial rise in the curve before the $NO/NO_2$ response is due to residual $NH_3$ in the gas line. The concentrations of the individual gases were NO—1,000 ppm; $C_3H_6$—1,000 ppm; CO—1,000 ppm; $NH_3$—100 ppm, 50 ppm, 25 ppm, 12 ppm, 6 ppm, 3 ppm, 1.5 ppm; $O_2$—17 vol %;

and $H_2O$—1.5 vol %; wherein the volumes are based upon the total volume of the combined gases, and the ppm are based upon the combined gases.

Example 3

Pt and $V_2O_5$ pastes were printed together and were fired at 800° C. for 10 minutes. Afterwards, the sensing elements were operated with the 7.5 V-1.06 amp (7.95 W) power supplied to the heater.

Example 4

$La_{0.8}Sr_{0.2}MnOx$ and $V_2O_5$ pastes were printed together and were fired at 800° C. for 5 minutes. Afterwards, the sensing elements were operated with the 8V-1.296 A (10.4 W) power supplied to the heater.

Example 5

$La_{0.6}Sr_{0.4}Fe_{0.8}Co_{0.2}Ox$ and $V_2O_5$ pastes were printed together and were fired at 800° C. for 10 minutes. Afterwards, the sensing elements were operated with the 7.5V-1.06 A (7.95 W) power supplied to the heater.

Example 6

$La_{0.6}Sr_{0.4}Fe_{0.8}Co_{0.2}Ox$ and $V_2O_5$ pastes were printed together and were fired at 800° C. for 10 minutes. Afterwards, the sensing elements were operated with the 7.0V-1.23 A (8.61 W) power supplied to the heater.

Example 7

LaCoOx and $V_2O_5$ pastes were printed together and were fired at 800° C. for 10 minutes. Afterwards, the sensing elements were operated with the 7.5V-1.244 A (9.33 W) power supplied to the heater.

Example 8

$Bi_{1.84}Pb_{0.34}Sr_{1.91}Ca_{2.03}Cu_{3.06}Ox$ and $V_2O_5$ pastes were printed together and were fired at 700° C. for 10 minutes. Afterwards, the sensing elements were operated with the 6 V-1.17 amp (7.02 W) power supplied to the heater.

Example 9

$La_{0.8}Ca_{0.2}CrOx$ and $V_2O_5$ pastes were printed together and were fired at 750° C. for 5 minutes. Afterwards, the sensing elements were operated with the 7.5 V-1.24 amp (9.30 W) power supplied to the heater.

Example 10

$Bi_2Sr_2CaCuOx$ and $V_2O_5$ pastes were printed together and were fired at 700° C. for 10 minutes. Afterwards, the sensing elements were operated with the 8 V-1.07 amp (8.56 W) power supplied to the heater.

Example 11

NiO and $V_2O_5$ pastes were printed together and were fired at 850° C. for 10 minutes. Afterwards, the sensing elements were operated with the 8 V-1.07 amp (8.56 W) power supplied to the heater.

Example 12

Pt and $V_2O_5$ pastes were printed together and were fired at 800° C. for 10 minutes. Afterwards, the sensing elements were operated with the 7 V-1.25 amp (8.75 W) power supplied to the heater.

Examples 13-15 illustrate examples of the type of ammonia selective sensing electrode comprising $V_2O_5$ with CaO, SrO, SnO, PbO, CuO, $Sb_2O_3$, $Bi_2O_3$, $Nb_2O_5$, $Ta_2O_5$, $CrO_3$, $WO_3$, $MoO_3$, with electrical conducting metal and/or metal oxide materials.

Example 13

Au, $V_2O_5$, and $Sb_2O_3$ pastes were printed together and were fired at 700° C. for 10 minutes. Afterwards, the sensing elements were operated with the 7 V-1.15 amp (8.05 W) power supplied to the heater.

Example 14

Au, $V_2O_5$, and $TiO_2$ pastes were printed together and were fired at 700° C. for 10 minutes. Afterwards, the sensing elements were operated with the 7V-1.16 A (8.12 W) power supplied to the heater.

Example 15

Au, $V_2O_5$, and $Bi_2O_3$, PbO, SrO, CaO, and CuO (1.84: 0.34:1.91:2.03:3.06) pastes were printed together and were fired at 850° C. for 10 minutes. Afterwards, the sensing elements were operated with the 7 V-1.19 amp (8.33 W) power supplied to the heater.

Examples 16 and 17 illustrate yet another type of ammonia selective sensing electrode comprising a compound of V (such as $BiVO_4$, $Cu_2(VO_3)_2$, and the like), with electrical conducting metal and/or metal oxide materials.

Example 16

Au and $Cu(VO_3)_2$ pastes were printed together and were fired at 800° C. for 10 minutes. Afterwards, the sensing elements were operated with the 7 V-1.17 amp (8.19 W) power supplied to the heater.

Example 17

$Bi_2Sr_2CaCu_2Ox$ and $Cu(VO_3)_2$ pastes were printed together and were fired at 400° C. for 10 minutes. Afterwards, the sensing elements were operated with the 5.5 V-1.16 amp (6.38 W) power supplied to the heater.

Examples 18 and 19 illustrate yet another type of ammonia selective sensing electrode comprising $WO_3$ and/or $MoO_3$ with electrical conducting metal and/or metal oxide materials.

Example 18

$La_{0.79}Sr_{0.2}FeOx$ and $WO_3$ pastes were printed together and were fired at 800° C. for 10 minutes. Afterwards, the sensing elements were operated with the 7 V-1.41 amp (9.87 W) power supplied to the heater.

Example 19

Au and $MoO_3$ pastes were printed together and were fired at 750° C. for 1 hour. Afterwards, the sensing elements were operated with the 7 V-1.23 amp (8.61 W) power supplied to the heater.

The results of Examples 3-19 are set forth in Table 1.

TABLE 1

| Response for Example Nos. | GAS | | | |
|---|---|---|---|---|
| | $NO/NO_2$ (1,000 ppm) | $C_3H_8/C_3H_6$ (1,000 ppm) | CO (1,000 ppm) | $NH_3$ (100 ppm) |
| 3 (mV) | 6.31 | 25.5 | 13 | 59.6 |
| 4 (mV) | −3.3 | 0.8 | −4.6 | 30.8 |
| 5 (mV) | 1.2 | −0.6 | −0.7 | 30.1 |
| 6 (mV) | 0.7 | −4.7 | −3.1 | 99.8 |
| 7 (mV) | 6.5 | 3.5 | 2.8 | 534.0 |
| 8 (mV) | 1.02 | 3.16 | 2.95 | 136.6 |
| 9 (mV) | 4.68 | −1.05 | −3.8 | 73.01 |
| 10 (mV) | 14.33 | 1.68 | 0.68 | 54.53 |
| 11 (mV) | −17 | −15 | −16 | 132 |
| 12 (mV) | −2.57 | 0.89 | 3.28 | 82.44 |
| 13 (mV) | 19.5 | −9.5 | −6.7 | 90.3 |
| 14 (mV) | 12.1 | 2.7 | 1.2 | 98.6 |
| 15 (mV) | −0.57 | −1.23 | −0.15 | 71 |
| 16 (mV) | 7.9 | −2.6 | −1.4 | 36.8 |
| 17 (mV) | 16.45 | 0.98 | 1.03 | 57.33 |
| 18 (mV) | 12.62 | 27.94 | 3.04 | 56.49 |
| 19 (mV) | 2.83 | −0.52 | −0.77 | 98.85 |

As can be seen from Table 1, the electrodes are sensitive to ammonia concentrations while being insensitive to NOx, HC, and CO in the gas. Particular note is taken of Examples 6-8, 12, 14, and 19. In these Examples, the voltages associated with the NOx, HC, and CO are very insignificant in relation to the voltage associated with the ammonia.

Some exemplary electrodes and test results are set forth in Table 2. For example, using $BiVO_4$ as the basic material, Mg (e.g., less than or equal to about 5 atomic percent (at %)) can be added to increase its electrical conductivity and to set the $NH_3$ sensing operation temperature around 600° C.-650° C. Ta and/or Nb (e.g., less than or equal to about 5 at % of each) can be added to chemically stabilize the compound (e.g., to reduce likelihood it will reduce and dissociate) and to lessen or eliminate the green effect (i.e., the changes of emf output at the first 24 hours of sensor operation to a constant $NH_3$ gas mixture). Pb, Zn, and/or Fe (e.g., less than or equal to about 0.5 at % of each) can also be added to inhibit the diffusion effect of these elements (e.g., when they enter the electrode as airborne exhaust impurities). Additionally, Zr and/or Y can be added (e.g., less than or equal to about 0.5 at % of each) to avoid the interaction with electrolyte material such as yttria doped zirconia (e.g., diffusion of either element into the electrode).

These electrodes can be made, for example, by combining $Bi_2O_3$, $V_2O_5$, and with the appropriate dopant (Mg, Ta, Zr, Zn, and/or Pb; see Table 2), e.g., by milling and/or grinding to form a mixture. The mixture was then fired at about 800° C. for overnight (i.e., for about 15 hours). The fired mixture was again be mixed (e.g., milled) prior to a second firing at 850° C. for about 15 hours and a final mixing (grinding by hand with a mortar and pestle for 5 minutes). Fewer mixing (e.g., one), and firing (again, one) processes can be employed if uniform mixing is attained initially. Alternatively, multiple steps can be employed to ensure the desired mixing and reaction between the components. The resultant material was then disposed onto the sensor by forming it into an ink (e.g., a liquid-solid mixed solution), and screen printing it onto an electrolyte.

TABLE 2

| Electrode | Conditions | Gas | | | |
|---|---|---|---|---|---|
| | | $NH_3$ 100 ppm (mV) | NO 1,000 ppm (mV) | HC 1,000 ppm (mV) | CO 1,000 ppm (mV) |
| $BiVO_4$ Dopant: | | | | | |
| Mg - 5 at % | 850° C. - 0.5 H | 126.9 | 29 | 19 | 6 |
| | 800° C. - 570 H | 138.7 | 34 | 26 | 11 |
| Mg/Ta - 5 at % | 850° C. - 0.5 H | 138.4 | 43 | 23 | 10 |
| | | 137.9 | | | |
| | 800° C. - 570 H | 154.9 | 69 | 53 | 40 |
| | 800° C. - 24 H | 151.4 | | | |
| Mg/Nb - 5 at % | 850° C. - 0.5 H | 115.6 | 20 | 12 | 3 |
| | 800° C. - 570 H | 144.2 | 56 | 39 | 22 |
| Mg/Ta 5 at %*; Zr 1 at %; Y/Zn/Pb 0.5 at % | 850° C. - 0.5 H | 111.7 | 20 | 12 | 4 |
| | 800° C. - 570 H | 136 | 36 | 32 | 20 |
| Mg/Nb 5 at %; Zr 1 at %; Y/Zn/Pb 0.5 at % | 850° C. - 0.5 H | 125 | 25 | 15 | 5 |
| | 800° C. - 570 H | 142.2 | 35 | 28 | 18 |

*i.e., the amounts are the total at % for those dopants; e.g., at % Mg + at % Nb = 5 at %.

Figure 9:
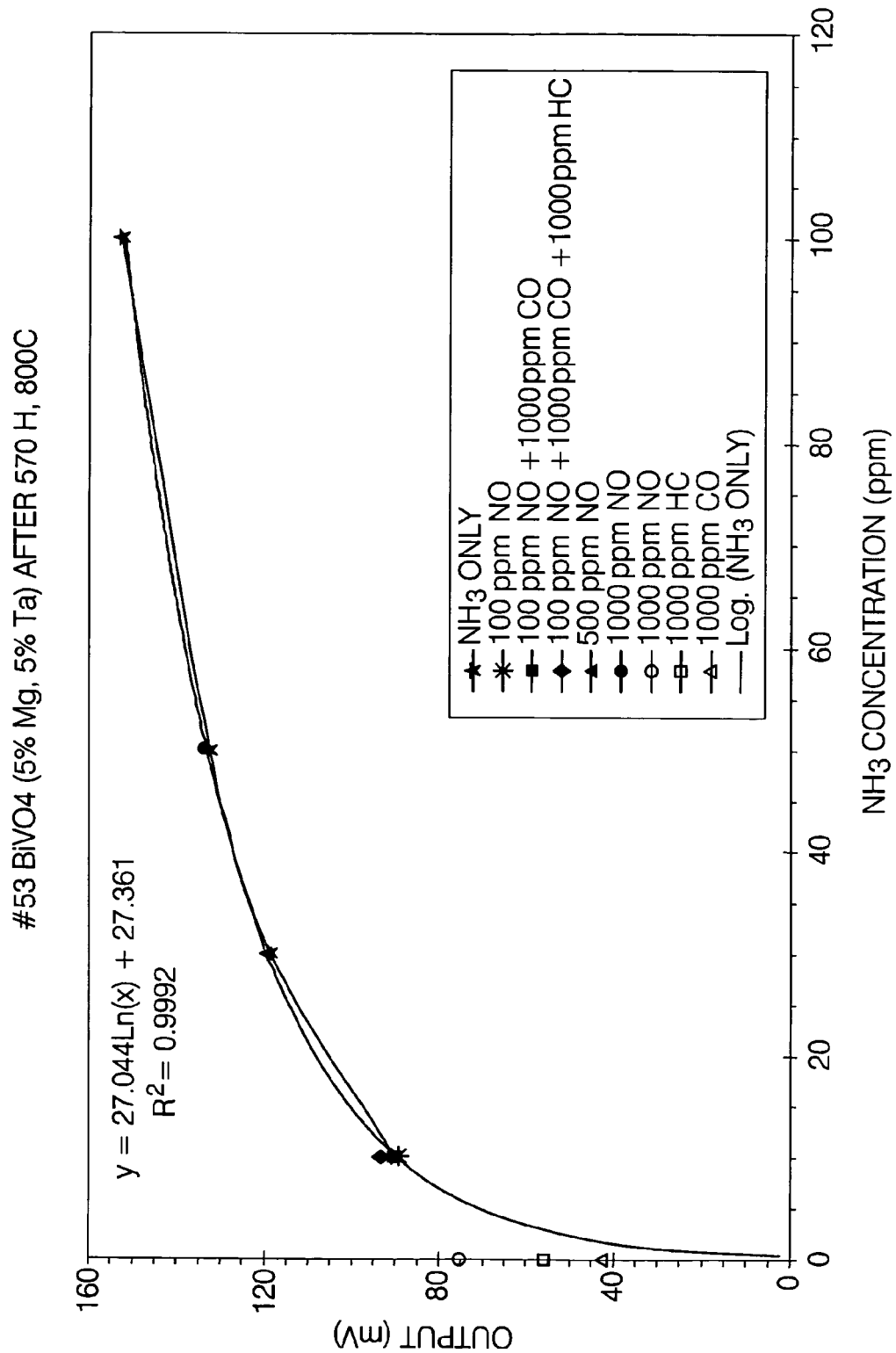
FIG. 9 is a graphical illustration of sensor emf outputs as function of $NH_3$ concentration and the presence of 1,000 ppm of CO, HC, and NO.

As is illustrated in Table 2, as the electrode ages, it can be seen that by employing the chemical stabilizing dopant, the aged electrode and the green electrode exhibit similar properties. For example, with the Mg/Ta dopant, the mV response changed from green (i.e., ≦about 24 hours of use), 151.4 mV, to aged, 154.9 mV; i.e., 2.3% change. Additionally, due to the use of the chemical stabilizing dopants, the mV reading of 100 ppm $NH_3$ will remain constant for the life of the sensor (e.g., will remain at 136 mV). The addition of Zr, Y, Pb, and Zn in the above materials stabilized the material such that the electrode was less likely to be poisoned by these elements through the diffusion process, after these materials are attached to the electrodes (e.g., during use). The presence of HC, CO, and NO will not interfere with the NH$_3$ sensing, as shown in FIG. 9. As shown in this figure, as zero NH$_3$, although there is emf response to CO, HC, NO, the NH$_3$ measurement is not influenced.

In prior methods for monitoring ammonia gas, such as those based on optical principles, problems exist with humidity, high temperature, slow response time, aging effect, CO and hydrocarbon interference effect, manufacturing difficulties, and high cost. The disclosed ammonia gas sensor is reliable for monitoring ammonia concentrations of about 1 ppm to about 100 ppm and above. It operates reliably in concentrations of water vapor of about 0.5 vol % to 12 vol %. It is economically-produced and operated. The disclosed sensor is characterized by quick response time (e.g., less than or equal to about 1 second), and operates over a wide range of temperatures (e.g., temperatures of about 140° C. to about 700° C.).

The present ammonia gas sensor provides many advantages. The electrodes are selectively sensitive to ammonia, and therefore can accurately determine ammonia concentration in an exhaust gas. The sensor is economical to manufacture and to operate. Due to the combination of materials in the sensing formulation, the sensor resists the green effect (i.e., maintains a mV reading, through the first 100 hours of operation, that varies by ±5%), and is resistant to poisoning from the materials of the electrode, as well as air borne contaminants. Additionally, it is easily portable and can be used for pollution monitoring and control in ambient air, indoors or outdoors, in engine exhaust systems, in combustor flues, and elsewhere.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. An ammonia gas sensor, comprising:
   an electrolyte;
   a reference electrode in contact with the electrolyte; and
   an ammonia selective sensing electrode in contact with the electrolyte spaced apart from the reference electrode, said ammonia selective sensing electrode composed of an oxide material characterized by the formula $A_xM_yO_z$ wherein M is selected from the group consisting of vanadium, tungsten, and molybdenum;
   wherein A is one or more metals; and
   wherein x, y and z are non-zero numbers indicative of the atomic proportion.

2. The ammonia gas sensor in accordance with claim 1, wherein the electrolyte is composed of a material capable of electrochemical transfer of hydrogen ions.

3. The ammonia gas sensor in accordance with claim 2, wherein the electrolyte is a zirconia composition.

4. The ammonia gas sensor in accordance with claim 3, wherein the zirconia composition comprises zirconia containing an additive adapted to stabilize the zirconia at elevated temperatures.

5. The ammonia gas sensor in accordance with claim 4, wherein the electrolyte is yttria-stabilized zirconia.

6. The ammonia gas sensor in accordance with claim 1, wherein A includes a metal selected from the group consisting of bismuth, lead, lanthanum, strontium, calcium, copper, gadolinium, neodymium, yttrium, samarium, and magnesium.

7. The ammonia gas sensor of claim 6, wherein A is between about 0.1 at % to about 15 at %.

8. The ammonia gas sensor of claim 6, wherein A is between about 1 at % to about 10 at %.

9. The ammonia gas sensor of claim 6, wherein A is between about 3 at % to about 8 at %.

10. The ammonia gas sensor in accordance with claim 1, wherein the oxide material further comprises a chemically stabilizing dopant.

11. The ammonia gas sensor in accordance with claim 10, wherein the chemically stabilizing dopant is selected from the group consisting of tantalum, niobium, and magnesium.

12. The ammonia gas sensor of claim 10, wherein the chemically stabilizing dopant is between about 0.1 at % to about 5 at %.

13. The ammonia gas sensor of claim 10, wherein the chemically stabilizing dopant is between about 0.3 at % to about 3 at %.

14. The ammonia gas sensor in accordance with claim 1, wherein the oxide material further comprises a diffusion-impeding dopant.

15. The ammonia gas sensor in accordance with claim 14, wherein the diffusion-impeding dopant is selected from the group consisting of zinc, zirconium, lead, iron, and yttrium.

16. The ammonia gas sensor in accordance with claim 1,
    wherein M is vanadium; and
    wherein A is selected from the group consisting of bismuth, lead, lanthanum, strontium, calcium, copper, gadolinium, neodymium, yttrium, samarium, magnesium, tin, antimony, neodymium, tantalum and chromium.

17. The ammonia gas sensor of claim 16, wherein A comprises bismuth.

18. The ammonia gas sensor in accordance with claim 16, wherein A further comprises a chemically stabilizing dopant selected from the group consisting of tantalum and magnesium.

19. The ammonia gas sensor in accordance with claim 16, wherein A further comprises a diffusion-impeding dopant selected from the group consisting of zinc, zirconium, lead, iron, and yttrium.

20. A process for measuring the concentration of ammonia in a gas, the process comprising
    providing an ammonia gas sensor comprising an electrolyte, a reference electrode in contact with the electrolyte; and an ammonia selective sensing electrode in contact with the electrolyte spaced apart from the reference electrode, said ammonia selective sensing electrode composed of an oxide material characterized by the formula $A_xM_yO_z$ wherein M is selected from the group consisting of vanadium, tungsten, and molybdenum;
    wherein A is one or more metals; and
    wherein x, y and z are non-zero numbers indicative of the atomic proportion;

contacting the gas with the ammonia selecting sensing electrode; and measuring a voltage signal between said ammonia sensing electrode and said reference electrode.

21. The process in accordance with claim 20, wherein the electrolyte is composed of a material capable of electrochemical transfer of hydrogen ions.

22. The process in accordance with claim 21, wherein the electrolyte is a zirconia composition.

23. The process in accordance with claim 22, wherein the zirconia composition comprises zirconia containing an additive adapted to stabilize the zirconia at elevated temperatures.

24. The process in accordance with claim 23, wherein the electrolyte is yttria-stabilized zirconia.

25. The process in accordance with claim 20, wherein A includes a metal selected from the group consisting of bismuth, lead, lanthanum, strontium, calcium, copper, gadolinium, neodymium, yttrium, samarium, and magnesium.

26. The process of claim 20, wherein A is between about 0.1 at % to about 15 at %.

27. The process of claim 20, wherein A is between about 1 at % to about 10 at %.

28. The process of claim 20, wherein A is between about 3 at % to about 8 at %.

29. The process in accordance with claim 20, wherein A comprises a chemically stabilizing dopant.

30. The process in accordance with claim 20, wherein the chemically stabilizing dopant is selected from the group consisting of tantalum, niobium, and magnesium.

31. The process of claim 30, wherein the chemically stabilizing dopant is between about 0.1 at % to about 5 at %.

32. The process of claim 30, wherein the chemically stabilizing dopant is between about 0.3 at % to about 3 at %.

33. The process in accordance with claim 20, wherein A comprises a diffusion-impeding dopant.

34. The process in accordance with claim 33, wherein the diffusion-impeding dopant is selected from the group consisting of zinc, zirconium, lead, iron, and yttrium.

35. The process in accordance with claim 20, wherein M is vanadium; and wherein A is selected from the group consisting of bismuth, lead, lanthanum, strontium, calcium, copper, gadolinium, neodymium, yttrium, samarium, magnesium, tin, antimony, neodymium, tantalum and chromium.

36. The process of claim 35, wherein A is bismuth.

37. The process in accordance with claim 36, wherein the oxide material further comprises a chemically stabilizing dopant selected from the group consisting of tantalum and magnesium.

38. The process in accordance with claim 36, wherein the oxide material further comprises a diffusion-impeding dopant selected from the group consisting of zinc, zirconium, lead, iron, and yttrium.

* * * * *